(12) United States Patent
Zuckerman (10) Patent No.: US 9,320,332 B2
(45) Date of Patent: Apr. 26, 2016

(54) PORTABLE STORAGE APPARATUS THAT INCLUDES AN INTEGRATED ARRANGEMENT FOR CONVERTING THE APPARATUS TO A BED OR A CHAISE

(71) Applicant: Zeev Zuckerman, Great Neck, NY (US)

(72) Inventor: Zeev Zuckerman, Great Neck, NY (US)

( * ) Notice: Subject to any disclaimer, the term of this patent is extended or adjusted under 35 U.S.C. 154(b) by 0 days.

(21) Appl. No.: 13/905,968

(22) Filed: May 30, 2013

(65) Prior Publication Data

US 2013/0319809 A1    Dec. 5, 2013

Related U.S. Application Data

(60) Provisional application No. 61/653,246, filed on May 30, 2012, provisional application No. 61/655,165, filed on Jun. 4, 2012.

(51) Int. Cl.
| | |
|---|---|
| *A45C 9/00* | (2006.01) |
| *A45F 4/06* | (2006.01) |
| *A47C 17/82* | (2006.01) |
| *A47C 4/52* | (2006.01) |

(52) U.S. Cl.
CPC ... *A45C 9/00* (2013.01); *A45F 4/06* (2013.01); *A47C 4/52* (2013.01); *A47C 17/82* (2013.01)

(58) Field of Classification Search
CPC ..... A45F 4/06; A45F 2004/1026; A45F 4/04; A45F 4/08; A45C 9/00; A45C 2009/002; A45C 17/82; A47C 17/86; A47C 14/52; A47F 17/82

USPC .............. 190/1, 2; 224/155, 156; 5/626, 627, 5/114, 116
See application file for complete search history.

(56) References Cited

U.S. PATENT DOCUMENTS

| | | | | |
|---|---|---|---|---|
| 879,988 | A | * | 2/1908 | Thompson ........................ 5/112 |
| 1,005,709 | A | | 10/1911 | Jackson ........................... 190/2 |
| 1,049,850 | A | * | 1/1913 | Grabemhorst ........................ 5/1 |
| 1,120,480 | A | | 12/1914 | Haskes ............................ 190/2 |
| 1,243,092 | A | * | 10/1917 | Norberti ........................... 5/113 |
| 1,428,642 | A | | 9/1922 | Lambie et al. ................... 5/119 |
| 1,525,572 | A | | 2/1925 | Dodd |
| 1,733,916 | A | | 10/1929 | Spalding ......................... 190/2 |
| 2,842,189 | A | | 7/1958 | Gratt ............................ 297/227 |
| 3,223,300 | A | * | 12/1965 | Moore et al. .................. 224/156 |
| 3,326,337 | A | | 6/1967 | Bell ............................... 108/36 |
| 3,516,523 | A | | 8/1968 | Pemberton, Jr. |
| 3,846,855 | A | | 11/1974 | Peterson ......................... 5/114 |
| 3,933,164 | A | * | 1/1976 | Ness et al. ..................... 135/95 |
| 4,044,411 | A | | 8/1977 | Peterson ........................... 5/99 |

(Continued)

FOREIGN PATENT DOCUMENTS

| | | |
|---|---|---|
| AU | 1992024422 | 4/1993 |
| FR | 329476 | 8/1903 |

(Continued)

OTHER PUBLICATIONS

Notification of Transmittal of the International Search Report and the Written Opinion of the International Searching Authority, or the Declaration dated Dec. 12, 2013 issued in corresponding PCT International Application No. PCT/US12/00124.

*Primary Examiner* — Sue A Weaver
(74) *Attorney, Agent, or Firm* — Ostrolenk Faber LLP (57) ABSTRACT

A portable apparatus including a storage and a support arrangement that is convertible to a resting platform defined as a back pack or a suitcase.

14 Claims, 13 Drawing Sheets

(56) References Cited

U.S. PATENT DOCUMENTS

| | | | |
|---|---|---|---|
| 4,056,857 A | 11/1977 | Quantz | 5/112 |
| 4,286,739 A * | 9/1981 | Silcott et al. | 224/156 |
| 4,511,071 A * | 4/1985 | Curran | 224/156 |
| 4,742,900 A | 5/1988 | Boxhammer | 190/2 |
| 4,802,249 A | 2/1989 | Bills | 5/420 |
| 4,856,627 A | 8/1989 | Polatov | 190/11 |
| 4,883,206 A | 11/1989 | Miller | 224/153 |
| 5,176,422 A | 1/1993 | Canet | 297/17 |
| 5,265,289 A | 11/1993 | Swiger et al. | 5/111 |
| 5,384,926 A * | 1/1995 | Al-Bargi | 5/627 |
| 5,551,558 A | 9/1996 | Bureau | 206/223 |
| 5,611,414 A | 3/1997 | Walker | 190/2 |
| 5,957,349 A | 9/1999 | Krulik | 224/155 |
| 6,174,026 B1 | 1/2001 | Wise | 297/120 |
| 6,655,736 B1 | 12/2003 | Arenas | 297/229 |
| 6,687,928 B1 | 2/2004 | Wilson | 5/99.1 |
| 6,851,139 B2 | 2/2005 | Arason et al. | 5/159.1 |
| 7,058,997 B1 | 6/2006 | Klinger | 5/413 R |
| 7,097,017 B1 | 8/2006 | LaCrosse et al. | 190/8 |
| 7,451,709 B2 | 11/2008 | Swartfager et al. | 108/14 |
| 7,574,758 B2 | 8/2009 | Arason et al. | 5/159.1 |
| 7,717,309 B1 | 5/2010 | Lehmberg | 224/154 |
| 2002/0074251 A1 | 6/2002 | Hershberg | 206/315.1 |
| 2002/0170932 A1 * | 11/2002 | Higgins et al. | 224/156 |
| 2004/0140332 A1 * | 7/2004 | Blood, Jr. | 224/156 |
| 2007/0170219 A1 * | 7/2007 | Ballarta et al. | 224/645 |
| 2008/0135366 A1 | 6/2008 | Katz et al. | 190/18 A |
| 2010/0175960 A1 | 7/2010 | Moskowitz et al. | 190/11 |
| 2010/0252589 A1 | 10/2010 | Popescu | 224/155 |
| 2011/0056788 A1 | 3/2011 | Jackson | 190/2 |
| 2011/0108381 A1 | 5/2011 | Gibson | 190/11 |

FOREIGN PATENT DOCUMENTS

| | | |
|---|---|---|
| FR | 2834431 | 1/2002 |
| GB | 216920 | 6/1924 |
| GB | 382587 | 10/1932 |
| GB | 1 443 664 | 7/1976 |
| GB | 2 181 640 | 4/1987 |
| GB | 2244912 | 12/1991 |
| WO | WO 2008/092863 | 8/2008 |

* cited by examiner

Fig. 4A
FRONT ELEVATION
SCALE 2" = 1'-0"

Fig. 4B
RIGHT ELEVATION
SCALE 2" = 1'-0"

LEFT ELEVATION
SCALE 2" = 1'-0"
Fig. 4C

BACK ELEVATION
SCALE 2" = 1'-0"
Fig. 4D

PORTABLE STORAGE APPARATUS THAT INCLUDES AN INTEGRATED ARRANGEMENT FOR CONVERTING THE APPARATUS TO A BED OR A CHAISE

CROSS REFERENCE TO RELATED APPLICATIONS

This application is based on and claims priority to U.S. Provisional Application No. 61/653,246, filed May 30, 2012 and U.S. Provisional Application No. 61/655,165, filed Jun. 4, 2012, the entire contents of which are hereby incorporated by reference.

FIELD OF THE INVENTION

The present invention relates to a travel accessory such as a backpack or a suitcase.

BACKGROUND AND SUMMARY OF DISCLOSURE

U.S. patent application Ser. No. 13/047,556 (U.S. Patent Application Publication No. 2012/0222931) and PCT/US2012/000124 (hereafter "related applications" and incorporated by reference) both disclose a number of suitcases having arrangements that allow for the conversion of the suitcases to a chaise or a bed. Generally speaking, these applications disclose supports, each disposed at opposite sides of a suitcase section, which can be deployed so that the suitcase may be used as a bed or a chaise. When not in use, the supports are stored within the suitcase.

One of the proposed arrangements in the related applications employs telescopic supports which can be selectively collapsed (stored state) or longitudinally extended (deployed state) to provide support for a compliant and rollable fabric. The rollable fabric is stored around a spring loaded roller in a compartment residing in the suitcase section so that it may be pulled out (thereby loading the biasing spring) and connected to a support to realize a support arrangement at one side of the suitcase. The compliant fabric, when disengaged from the support, is automatically retracted and rolled around its associated roller due to the force stored in the biasing spring.

While the related applications disclose similar arrangements, disclosed herein are further novel features which result in new combinations as will be appreciated by those skilled in the art.

SUMMARY OF THE CLAIMED INVENTION

A portable storage apparatus according to the present invention includes a storage; and at least one support arrangement convertible to a resting platform, the support arrangement including a support arm and a compliant body.

In one preferred form, the at least one support arm is telescopically extendible/collapsible. The compliant body may be a fabric that is rolled around a roller.

In one embodiment, the at least one support arm includes a handle, and the compliant body is securely attached to the handle.

In another embodiment, the at least one support arm includes a handle, and the roller resides in the handle.

The storage may be a sack with shoulder straps defining a backpack. A rigid plate may be integrated with the sack.

The storage may be a suitcase.

Other features and advantages of the present invention will become apparent from the following description of the invention, which refers to the accompanying drawings.

DETAILED DESCRIPTION

Figure 1A:
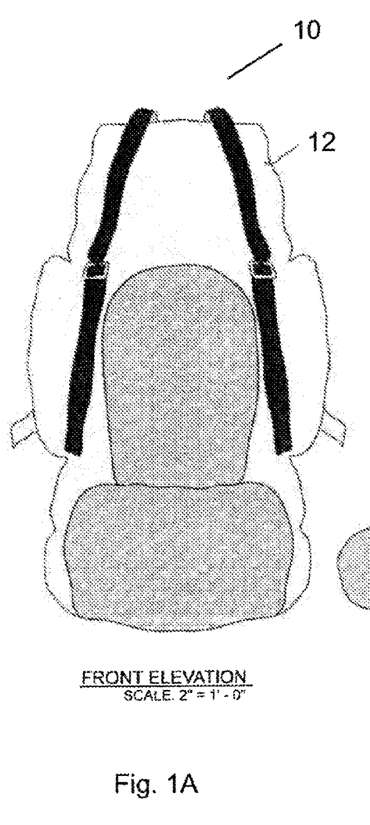
FIGS. 1A and 1B illustrate front and back elevation views, respectively, of a backpack according to the present invention.
Figure 1B:
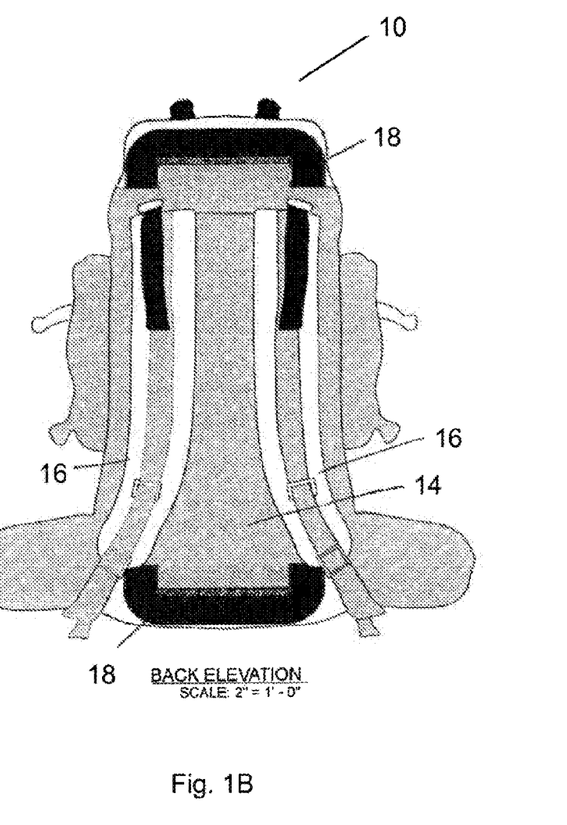

FIGS. 1A and 1B illustrate front elevation and back elevation views, respectively, of a backpack 10 that includes support arrangements, which can be deployed to convert the backpack into a resting platform such as a bed or a chaise. Backpack 10 includes a sack section 12 usually made of a fabric or the like material. On the side 14 configured for resting against the user's body (back side) are provided at least one, but usually two, shoulder straps 16. The manner of use of a backpack is well known. Therefore, how a backpack is used will not be described here.

FIGS. 1A and 1B illustrate the apparatus in a non-use state. Thus, the support arrangements are in a stored state. However, pull-out handles 18 are visible in FIG. 1B.

Figure 2A:
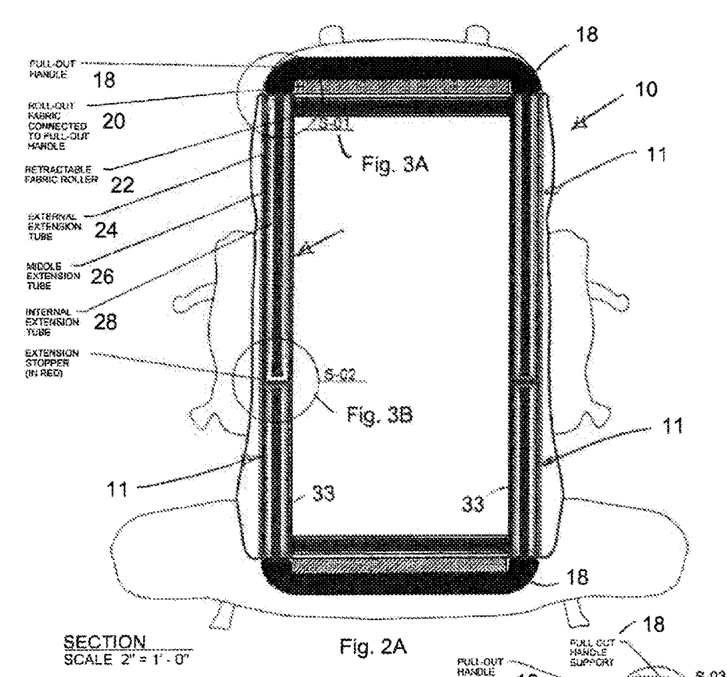
FIGS. 2A and 2B illustrate back and side elevation views, respectively, of a backpack according to the present invention.
Figure 2B:
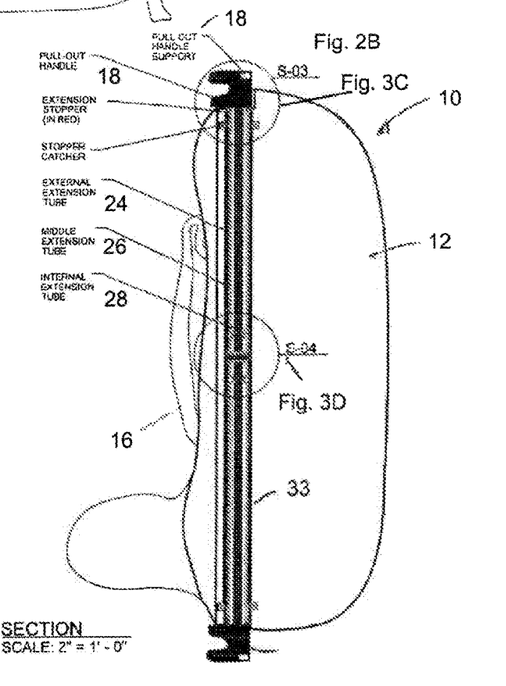

FIGS. 2A and 2B illustrate front and side elevation views, respectively, of backpack 10. For the sake of clarity, the sack section 12 and the shoulder straps 16 are only illustrated in outline form. A backpack 10 according to the invention includes at least one, but preferably two support arrangements. Each support arrangement includes a pull out handle 18, a compliant and rollable fabric 20, which, in its stored state, is rolled around a spring loaded roller 22 (similar to the one disclosed in the related applications discussed in the background section) and a pair of telescopic arms 11 each coupled to an end of pull out handle 18.

Each telescopic arm 11 includes an external extension tube 24 having a first internal diameter, a middle extension tube 26 having a second internal diameter smaller than the first internal diameter, and an internal extension tube (or rod) 28 having an outer diameter that is smaller than the first and the second internal diameters. Internal extension tube 28 is received inside of middle extension tube 26 and middle extension tube is received inside of external extension tube 24. Thus, internal extension tube 28 may be extracted from the interior of middle extension tube 26, and middle extension tube 26 may be extracted from the interior of external extension tube, whereby the three bodies can be extended/collapsed in a telescopic fashion.

Figure 3A:
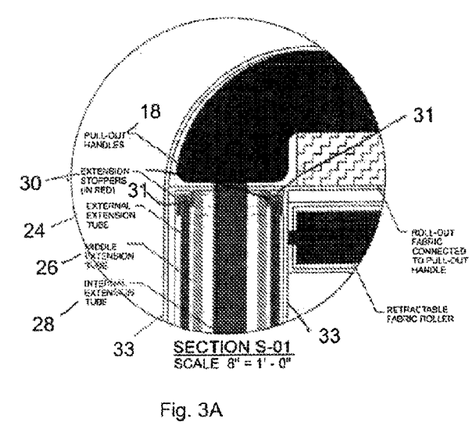
FIGS. 3A-3D illustrate sections identified in FIGS. 2A and 2B, namely, sections S-01, S-02, S-03, S-04.
Figure 3B:
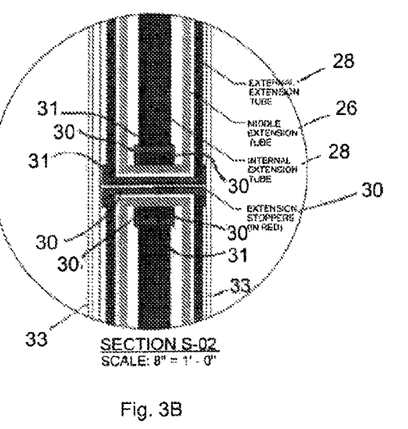
Figure 3C:
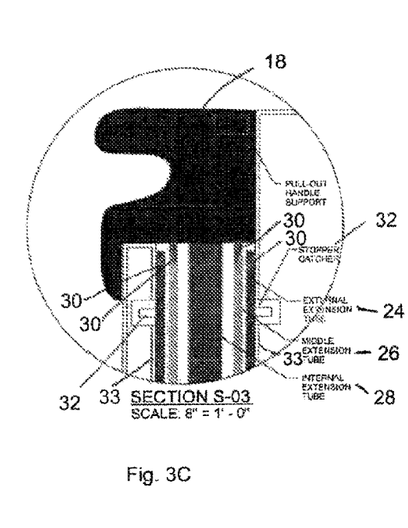
Figure 3D:
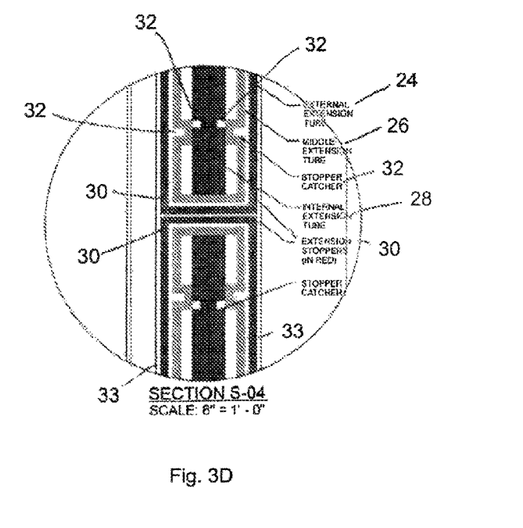

Referring to FIGS. 3A-3D, in order to integrate tubes 24-28, appropriate stoppers may be employed. Referring to FIG. 3A (identified as region S-01 in FIG. 2A), a pair of extension stoppers 30 are provided at the end of external extension tube 24. Extension stoppers 30 are configured to engage a section of middle extension tube 26 when middle extension tube 26 has been extended out a predetermined distance. Thus, for example, each extension stopper 30 may be pivotably mounted about a pin 31 (see FIG. 3C) allowing the stoppers 30 to swing into features defined in internal extension tube 24. Referring to FIG. 3D, for example, middle extension tube 26 may be provided with stopper catcher 32 recesses at a short distance from an end thereof. When middle extension tube 24 has been pulled out far enough extension stoppers 30 swing into stopper catchers 32 of middle extension tube 26 and prevent its further longitudinal travel. Note that the same mechanism is preferably used to stop the internal extension tube 28 from advancing beyond a predetermined point. Specifically, extension stoppers 30 are provided at the end of middle extension tube 26 in the same manner as described above, and internal extension tube 28 is provided with stopper catcher 32 recesses (see FIG. 3D) which engage extension stoppers 30 at the end of middle extension tube 26 when internal extension tube 28 has been pulled out far enough. Note that the end of internal extension tube 28 is coupled to pull out handle 18. Thus, when pull out handle 18 is pulled away from sack 12, internal extension tube 28 is extracted causing the telescopic extension of the tubes. Further note that external extension tube 24 includes extension stopper 30 (see FIGS. 3B and 3D), which pivot about pivot pin (see FIG. 3B), and are received inside respective stopper catch 32 recesses, deployed in a common support tube 33 which houses the telescopic arms. Common support tube 33 may be longitudinally aligned with tubes 24, 26 and 28, and disposed on or inside sack 12 backpack 10. One purpose of common support tube 33 is to set how far out external extension tube 24 may be extended outwardly, thereby setting the limit for the length of the telescopic arm 11 in its extended state.

Figure 3E:
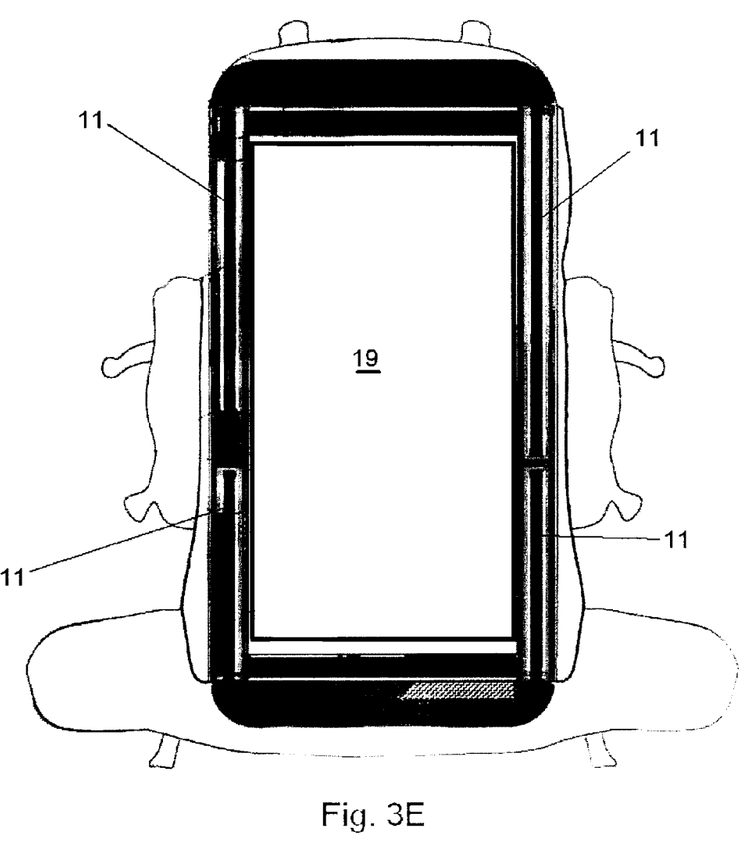
FIG. 3E illustrates a backpack according to a variation of the present invention.
Figure 4A:
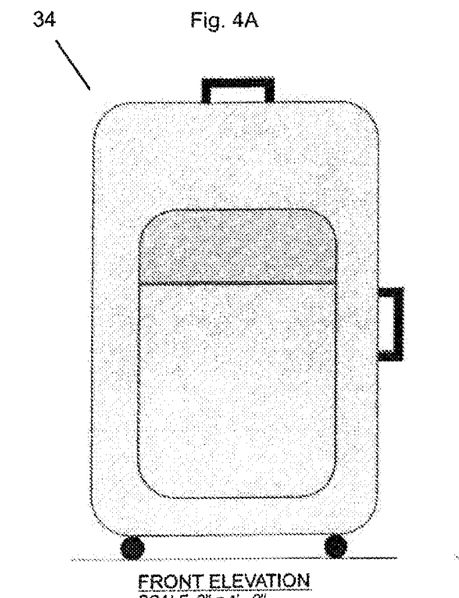
FIGS. 4A, 4B, 4C, and 4D illustrate front, right, left, and back elevation views, respectively, of a suitcase according to the present invention.
Figure 4B:
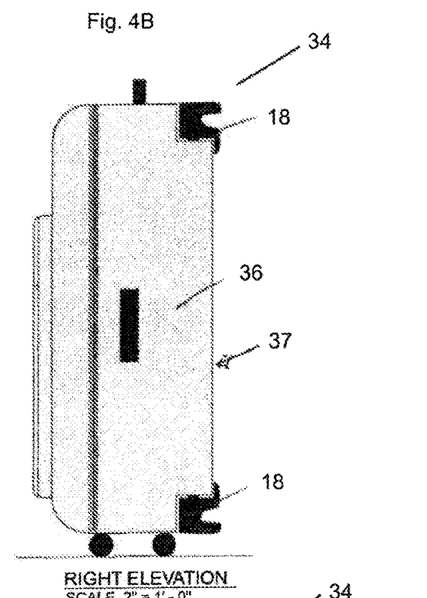
Figure 4C:
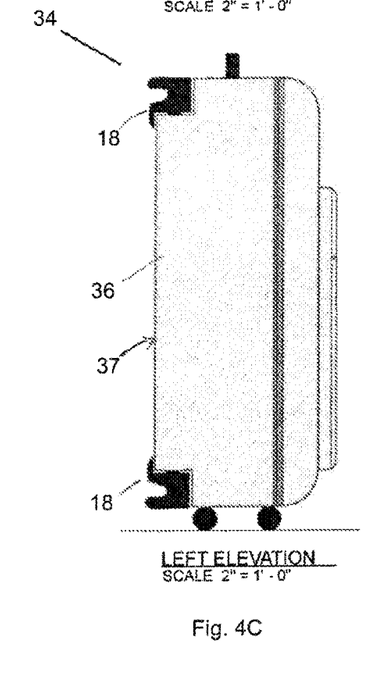
Figure 4D:
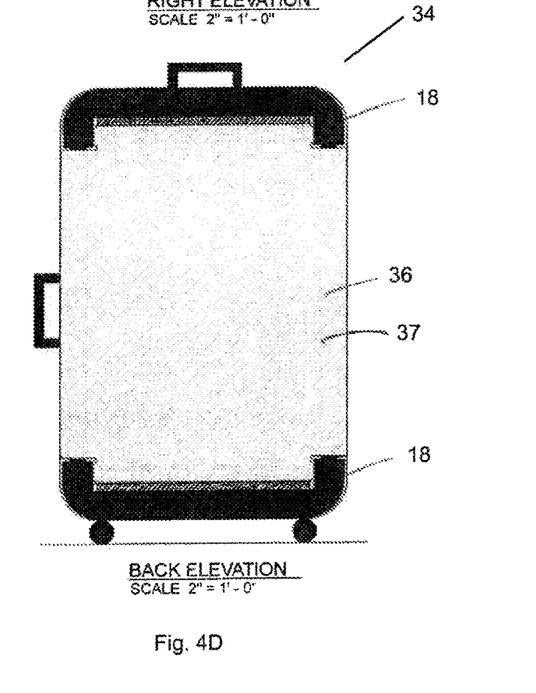

Referring now back to FIGS. 2A and 2B, while only one telescopic arm 11 has been described, it should be noted that two telescopic arms 11 are used to realize a support arrangement. Each telescopic arm 11 is positioned adjacent (i.e. close to) a respective side of two opposite sides of sack 12 in order to set the width of the support arrangement. Furthermore, while one support arrangement may be employed in a backpack 10 according to the present invention, two support arrangements, each deployable from a respective side of two opposite sides of sack 12, is preferred. Note that the telescopic support arms of each support arrangement may be extended to the same length, or different lengths, or may be configured to be the same or different length when stored. While not shown in the figures, it will be understood that to use the present invention, the user will extend the telescopic arms by pulling out the handle 18. The rollout fabric 20, which may be coupled to pull out handle 20, will be automatically pulled out (i.e., rolled out). Once telescopic arms 11 are fully extended, fabric 20 will provide a support for the user in generally the same manner as described in the related applications set forth in the background section. Note that, optionally, a rigid plate 19 or the like (FIG. 3E) may be integrated with sack portion 12 between arms 11 at back side of sack 12 to provide further support for the weight of the user. Preferably, the rigid plate is coupled to common support tubes 33, but such coupling is not necessary and the rigid plate may be left uncoupled.

FIGS. 4A, 4B, 4C and 4D show front, right, left and back elevation views of a suitcase 34 that includes the same support arrangements as those of backpack 10. Thus, instead of a sack 12, suitcase 34 includes a suitcase section 36 having one surface 37 which can provide, partial support for the user when the support arrangements are deployed, similar to the suitcases shown in the related applications discussed in the background section.

Figures 5A, 5B:
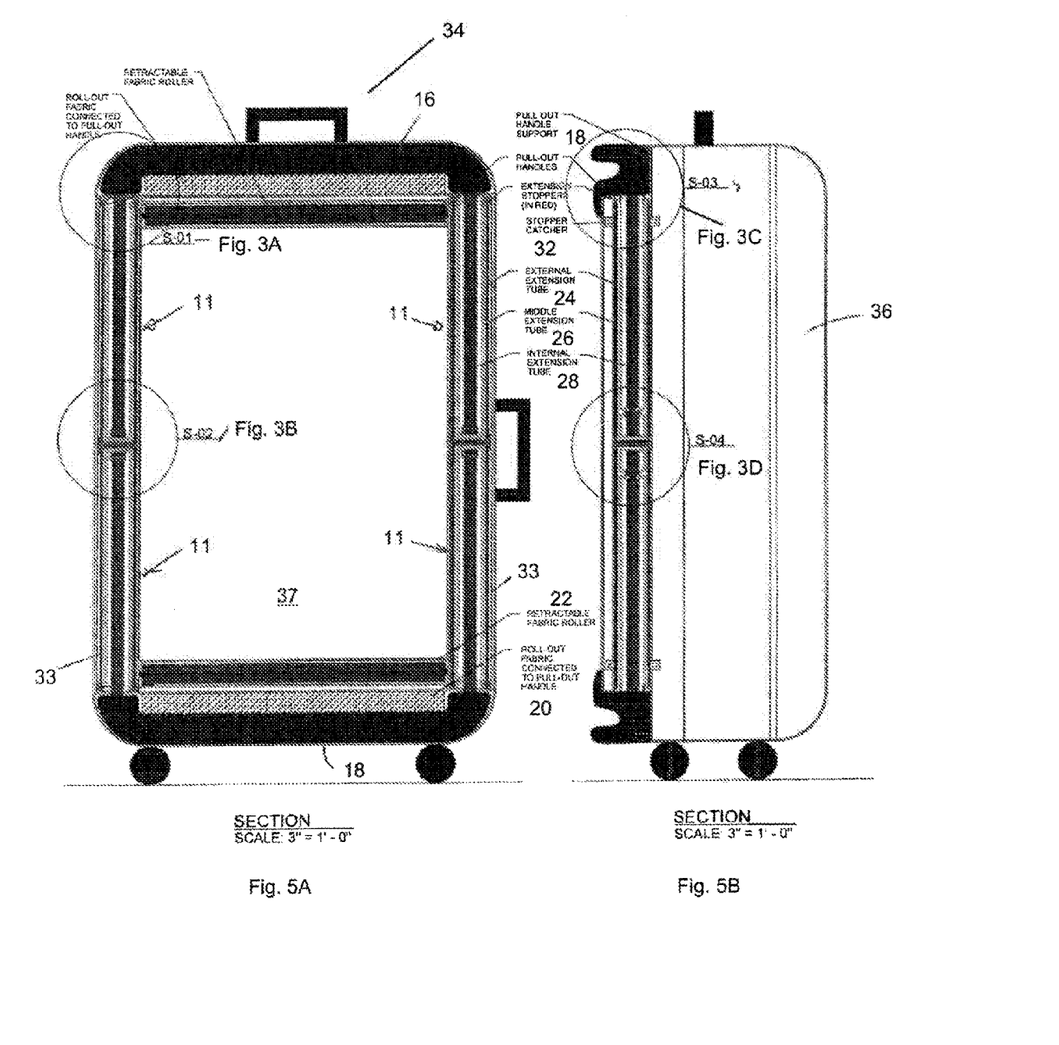
FIGS. 5A and 5B illustrate back and left elevation views of a suitcase according to the present invention.

FIGS. 5A and 5B illustrate suitcase 34. For the sake of clarity the suitcase section 36 is shown in outline form. Note that like numerals are used to identify like features as those described above.

Figure 6A:
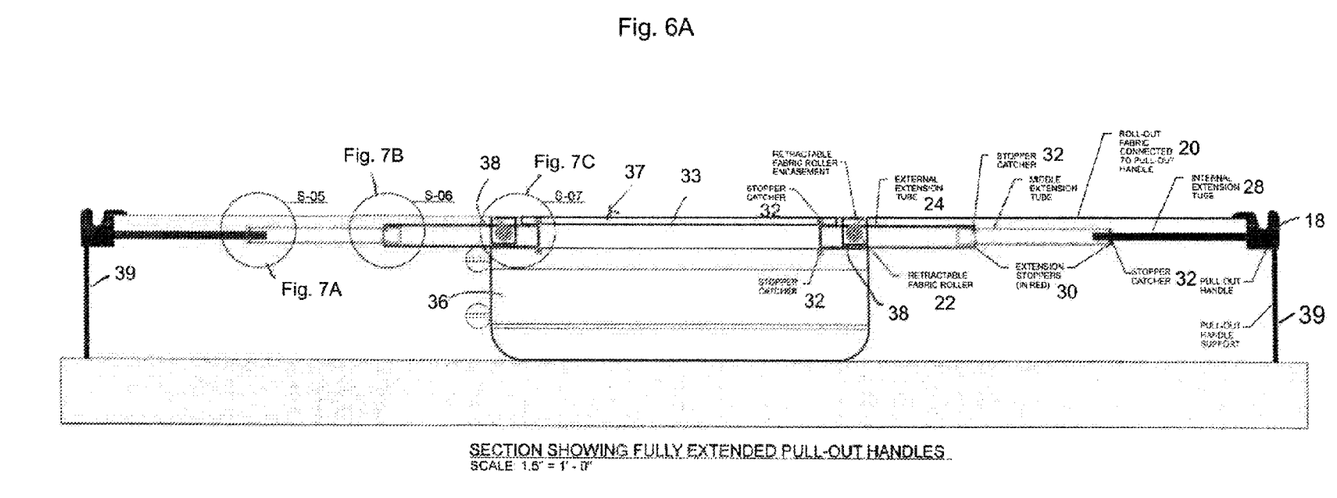
FIGS. 6A and 6B illustrate a suitcase according to the present invention with its support arrangements deployed.
Figure 6B:
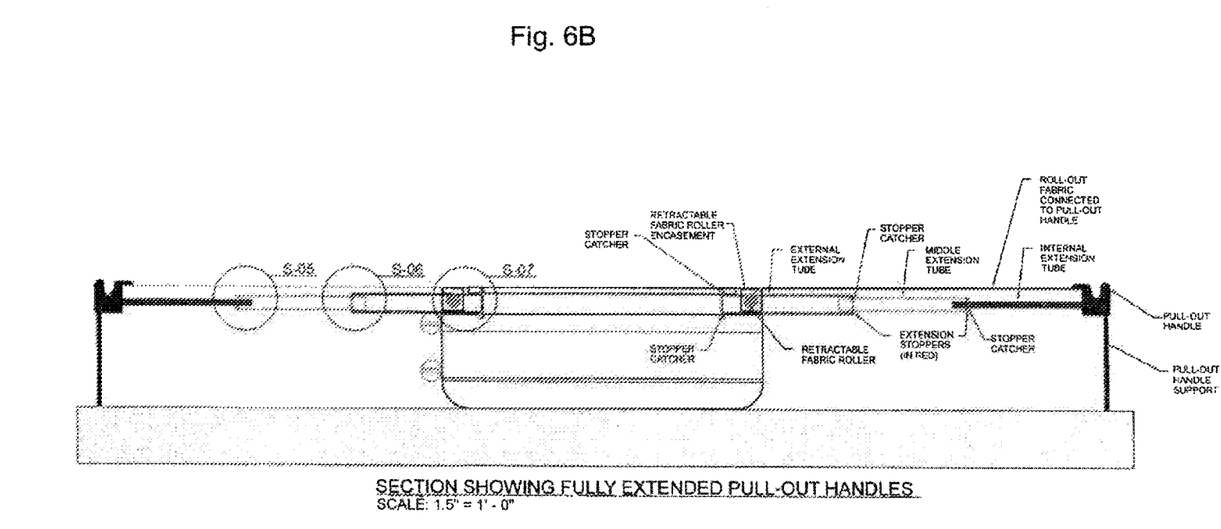

FIGS. 6A and 6B illustrate suitcase 34 with the support arrangements deployed for use. Note that a compartment 38 is provided inside suitcase section 36 to house fabric 20 and its associated roller. Such a component is also shown in the related applications discussed in the background section. Also, note a pull-out handle support 39, which is preferably hingedly coupled to handle 18, may be optionally provided for further support as also illustrated in the related applications described in the background section. Fabric 20 is permanently attached to handle 18; whereas, in the arrangements shown in the related applications described in the background section, the fabric is detachably attached.

Figure 7A:
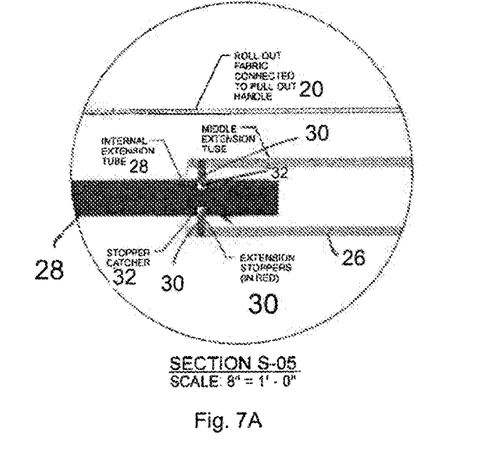
FIGS. 7A, 7B and 7C illustrate sections S-05, S-06 and S-07 identified in FIGS. 6A and 6B.
Figure 7B:
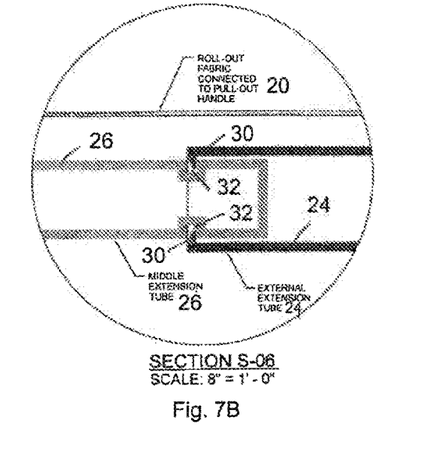
Figure 7C:
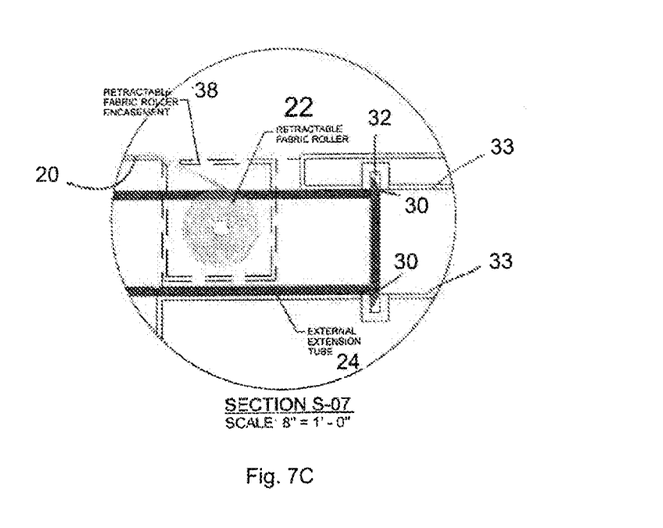
Figures 8A, 8B:
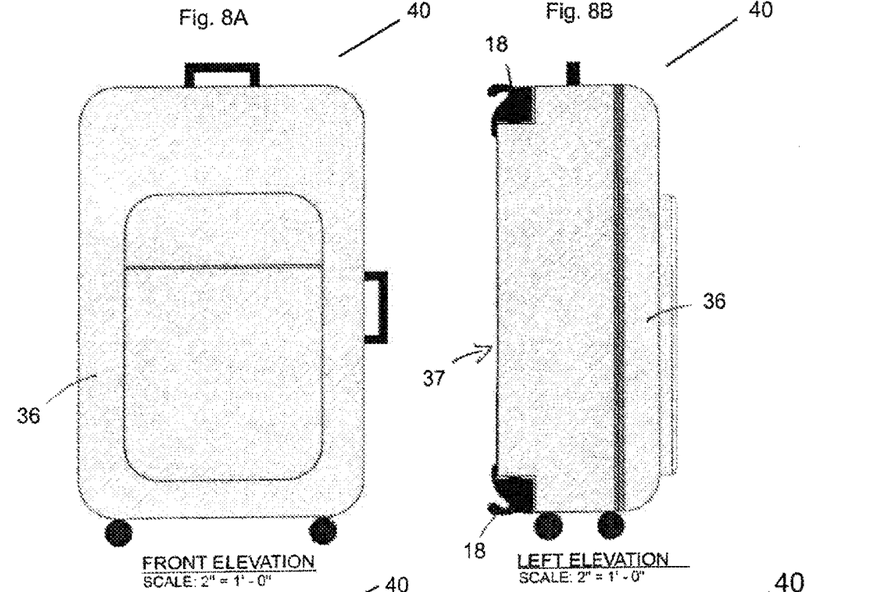
FIGS. 8A, 8B, 8C, and 8D illustrate front, right, left, and back elevation views, respectively, of a suitcase according to another variation of the present invention.
Figure 8C:
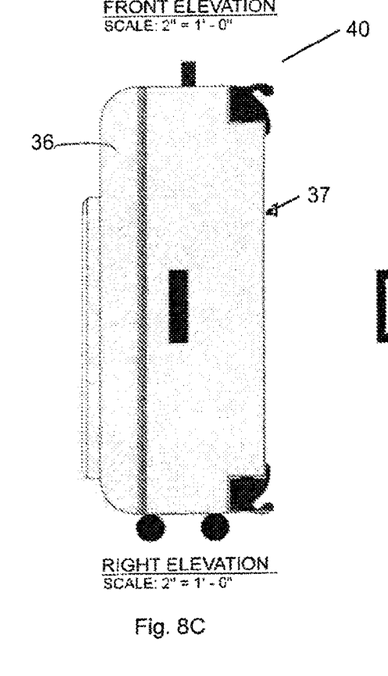
Figure 8D:
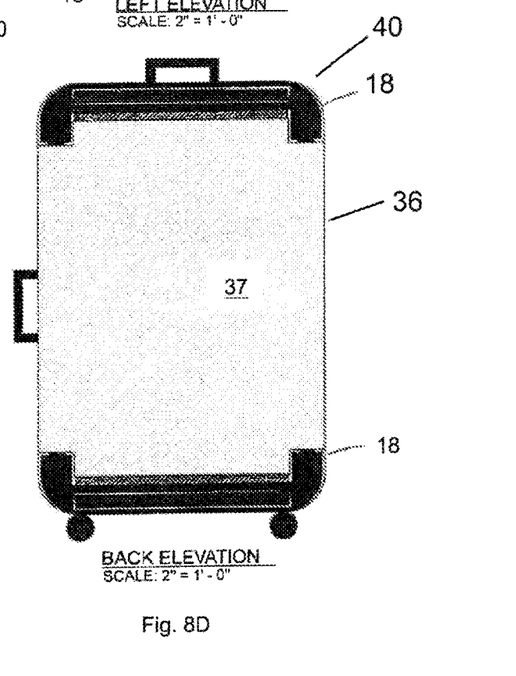

FIGS. 7A, 7B and 7C illustrate the stopper catcher arrangements described above in a deployed state.

FIGS. 8A, 8B, 8C and 8D show front, left, right and back elevation views, respectively, of a suitcase 40 according to a new variation. Suitcase 40 includes a suitcase section 36 having a surface 37 that can be used for partial support of a user. Similar to the backpack 10 and suitcase 34 and also similar to the suitcases shown in the related applications described in the background section, suitcase 40 includes support arrangements, which when deployed, convert the suitcase into a bed or a chaise. However, suitcase 40 employs a novel configuration.

Figure 9A:
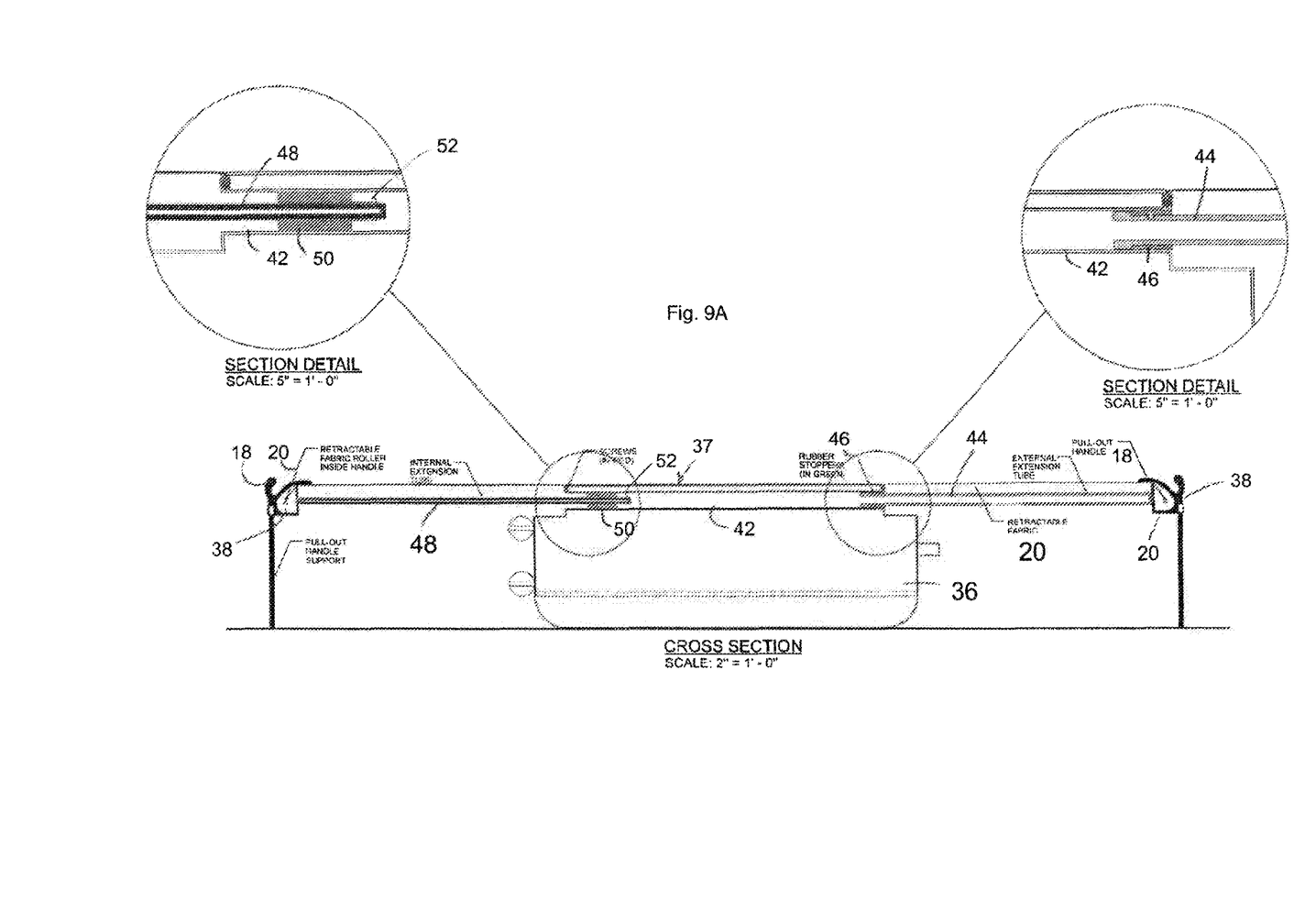
FIG. 9A illustrates a suitcase as depicted in FIGS. 8A-8D with its support arrangements in a deployed state.
Figures 9B, 9C:
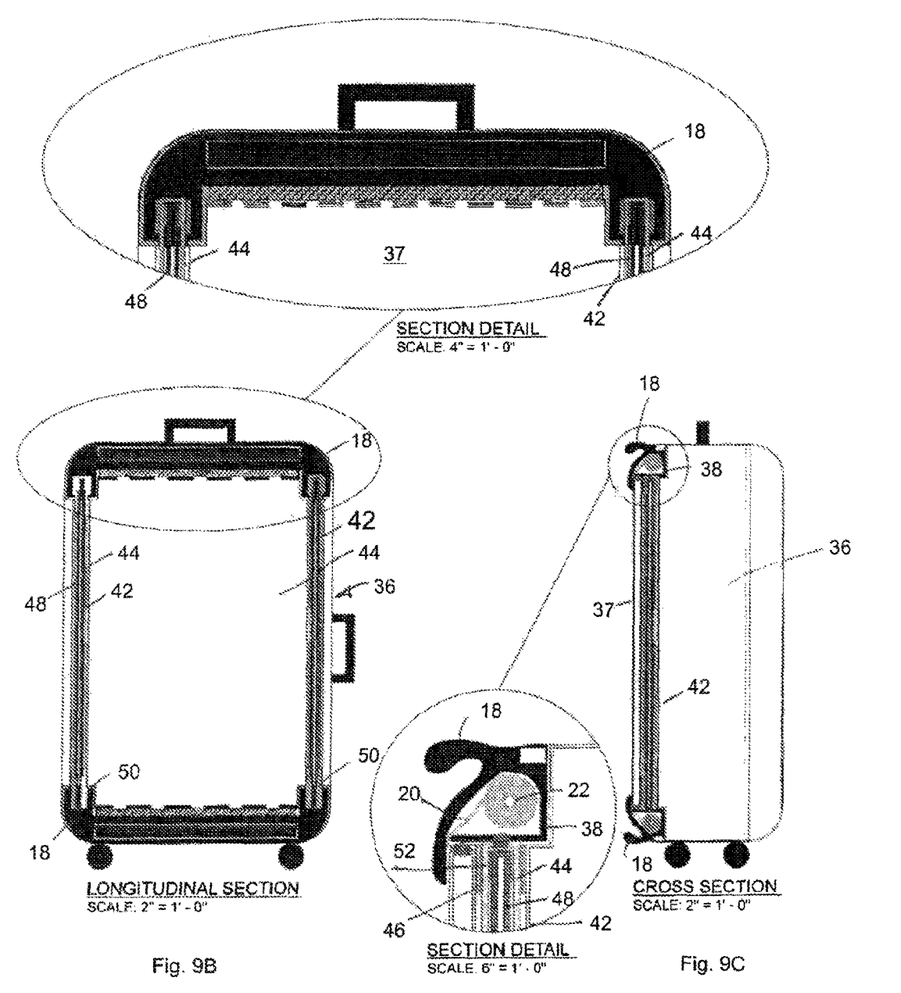
FIGS. 9B, 9C and 9D illustrate a suitcase as depicted in FIGS. 8A-8D and FIG. 9A with its support arrangements in a stored state.
Figure 9D:
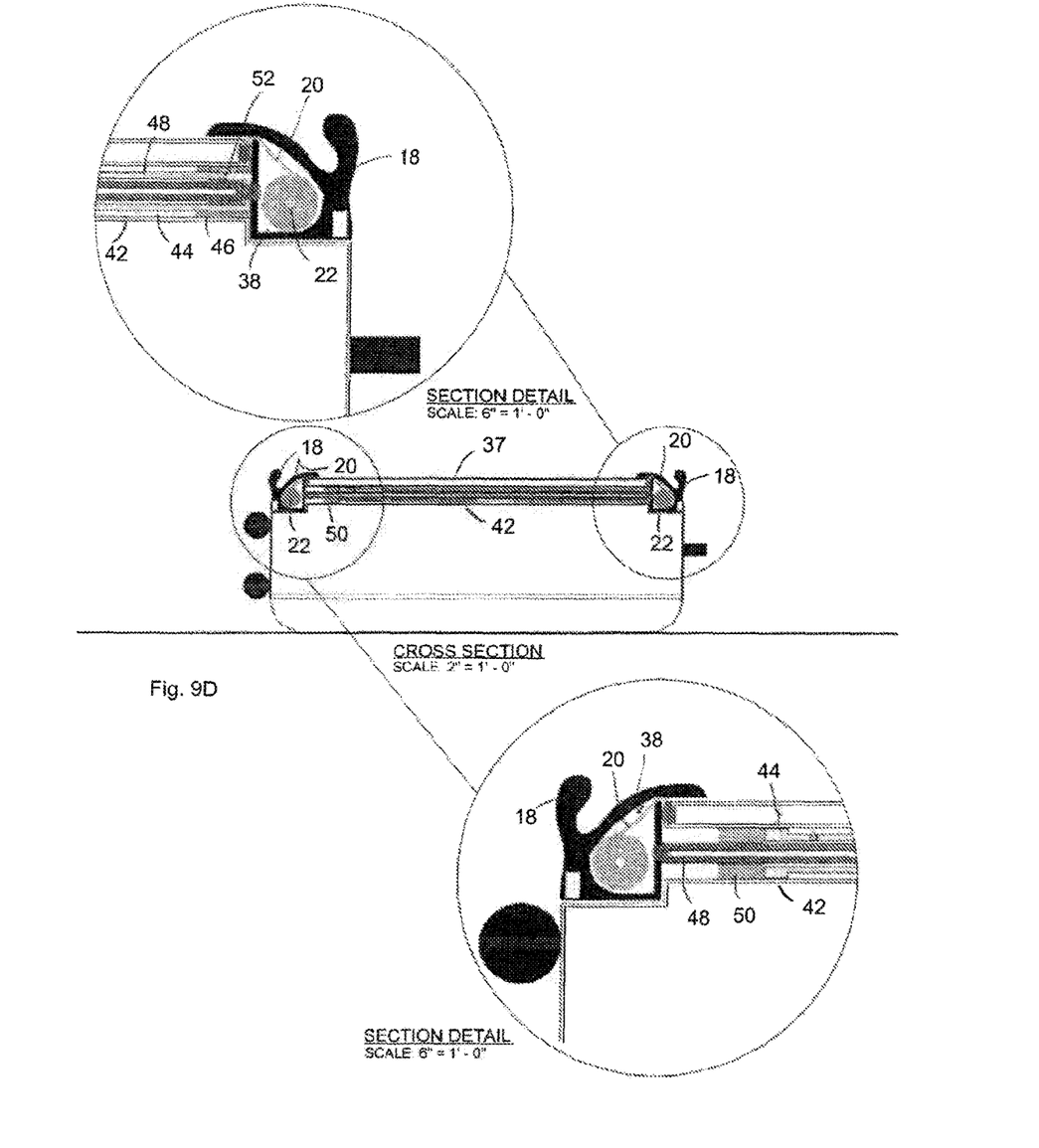

FIG. 9A illustrates suitcase 40 with the arrangements deployed. The support arrangements in suitcase 40 include a rollable fabric 20, a fabric roller 22, which is disposed in a compartment 38 residing at or inside handle 18, rather than at or inside suitcase section 36. Fabric 20 is permanently or detachably attached to suitcase section 36 at an edge which is adjacent to surface 37 of suitcase section 36. Note that suitcase 40 preferably includes two support arrangements each residing at one side of two opposite sides of suitcase section 36, each side being preferably adjacent surface 37. A support arrangement in suitcase 40 includes a one piece arm (not a multiple piece telescopic arm 11) which resides in and is slidably supported within a support tube 42. For example, one arm 44 is attached at one end to a handle 18, and is provided with a rubber stopper 46 at another, opposite end. Rubber stopper 46 is disposed on the exterior surface of arm 44 and is sized to make contact with the interior surface of support tube 42. Arm 44 may have a first interior diameter that is larger than the cross-section (exterior diameter) of another arm 48. Another arm 48 is coupled at one end to another handle 18 having another component 38 in which a roller 22 and fabric 20 reside (in a stored state), and includes another rubber stopper 50 at an opposite end. Rubber stopper 50 preferably extends around the exterior surface of arm 48 and is sized so that it makes contact with the interior surface of support tube 42. Note that in the stored state, arm 44 is received inside of support tube 44 until it meets rubber stopper 50, and arm 48 is moved, relative to rubber stopper 50 and received inside of arm 44 in the stored state. FIGS. 9B, 9C and 9D illustrate arms 44 and 48 in their stored state. Note that arm 48 may include a rubber top 52 or the like which is sized to engage the interior of arm 44 so that, in a stored state, arm 48 does not move around and cause rattling. Arm 44 is configured to slide relative to stopper 46, while stopper 46 is preferably fixed relative to support tube 42 and does not exit from support tube 42 when arm 44 is extracted. Similarly, arm 48 is configured to slide relative to stopper 50 while stopper 50 is preferably fixed relative to support tube 42 so that rubber stopper 50 does not exit support tube 42 when arm 48 is extended. Alternatively, stoppers 46 and 50 may be allowed to slide toward one another inside support tube 42; however, the respective ends of support tube 42 may be configured to prevent stoppers 46,50 from falling out of support tube 42. It should be noted that while only support arms 44 and 48 are discussed a each support arrangement, as illustrated in the figures, would include two support arms, each positioned adjacent a respective side of opposite sides of a suitcase section 36, and each connected at one end to a pull-out handle 18. Thus, one support arrangement would include two arms 44 each connected to a respective end of a pull-out handle 18 and another support arrangement would include a pair of arms 48 each connected at one end to a handle 18.

Although the present invention has been described in relation to particular embodiments thereof, many other variations and modifications and other uses will become apparent to those skilled in the art. It is preferred, therefore, that the present invention be limited not by the specific disclosure herein, but only by the appended claim.

What is claimed is:

1. A portable storage apparatus, comprising:
 a storage, wherein said storage is a sack and includes at least one shoulder strap at a back surface of the sack which is configured to rest against the user's body;
 at least a first support arrangement convertible to a resting platform, the support arrangement including (a) two telescopically extendible and parallel first support arms, each telescopically extendible first support arm including a first inner tube or rod, (b) a first handle connected to each first inner tube or rod, (c) a first roller extending between the first parallel support arms and located opposite said first handle; and (d) a first fabric rolled around the first roller and connected to the first handle; and
 two spaced common support tubes, each common support tube receiving a respective telescopically extendible first support arm, wherein the first handle is located adjacent the back surface and when moved rolls out said fabric.

2. The apparatus of claim 1, wherein said sack further comprises at least another shoulder strap at said back surface.

3. The apparatus of claim 1, further comprising a rigid plate integrated with said sack and disposed between said first support arms.

4. The apparatus of claim 1, further comprising at least a second support arrangement said second support arrangement including (a) two telescopically extendible and parallel second support arms, each telescopically extendible second support arm including a second inner tube or rod, (b) a second handle connected to each second inner tube or rod, (c) a second roller extending between the parallel second support arms; and (d) a second fabric rolled around the second roller and connected to the second handle.

5. The apparatus of claim 4, further comprising a rigid plate disposed between the first and the second support arms, wherein said second support arrangement is disposed opposite to said first support arrangement.

6. The apparatus of claim 5, wherein said support arms of said support arrangements are configured to support said first and said second fabrics.

7. The apparatus of claim 4, wherein each roller is spring loaded.

8. The apparatus of claim 1, wherein each telescopically extendible arm includes said inner tube or rod received in a middle extension tube, and an external extension tube, wherein said middle extension tube is received in said external extension tube and said external extension tube, said middle extension tube and said inner tube or rod are received in one of said common support tubes.

9. The apparatus of claim 1, further comprising a rigid plate residing between said first telescopically extendible support arms.

10. The apparatus of claim 1, wherein said common support tubes reside in said sack.

11. A portable storage apparatus, comprising:
 a sack;
 a shoulder strap at a back surface of the sack which is configured to rest against the user's body;
 a first support arrangement convertible to a resting platform, the first support arrangement including (a) two telescopically extendible and parallel first support arms, each telescopically extendible first support arm including a first inner tube or rod, (b) a first handle connected to each first inner tube or rod, (c) a first roller extending between the first parallel support arms; and (d) a first fabric rolled around the first roller and connected to the first handle;
 a second support arrangement convertible to a resting platform, the second support arrangement being disposed opposite said first support arrangement, the second support arrangement including (a) two telescopically extendible and parallel second support arms, each telescopically extendible second support arm including a second inner tube or rod, (b) a second handle connected to each second inner tube or rod, (c) a second roller extending between the second parallel support arms; and (d) a second fabric rolled around the second roller and connected to the second handle; and
 two spaced common support tubes, each common support tube receiving a respective telescopically extendible first support arm and a second telescopically extendible support arm, wherein said first handle and said second handle are located adjacent the back surface.

12. The apparatus of claim 11, further comprising a rigid plate positioned between said first arms and said second arms.

13. The apparatus of claim 11, wherein said common support tubes reside in said sack.

14. The apparatus of claim 11, wherein each telescopically extendible arm includes said inner tube or rod received in a middle extension tube, and an external extension tube, wherein said middle extension tube is received in said external extension tube and said external extension tube, said middle extension tube and said inner tube or rod are received in one of said common support tubes.

* * * * *